United States Patent
Mishra et al.

(10) Patent No.: US 9,535,046 B2
(45) Date of Patent: Jan. 3, 2017

(54) SOLID STATE SENSOR FOR DETECTION OF EXPLOSIVES

(71) Applicants: Indu B. Mishra, Scottsdale, AZ (US); William T. Petuskey, Phoenix, AZ (US)

(72) Inventors: Indu B. Mishra, Scottsdale, AZ (US); William T. Petuskey, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 265 days.

(21) Appl. No.: 14/090,335

(22) Filed: Nov. 26, 2013

(65) Prior Publication Data

US 2015/0285773 A1    Oct. 8, 2015

Related U.S. Application Data

(60) Provisional application No. 61/730,780, filed on Nov. 28, 2012.

(51) Int. Cl.
| | |
|---|---|
| *G01N 33/00* | (2006.01) |
| *G01N 27/12* | (2006.01) |
| *G01N 27/02* | (2006.01) |
| *C23C 16/30* | (2006.01) |
| *C23C 16/511* | (2006.01) |

(52) U.S. Cl.
CPC ......... *G01N 33/0057* (2013.01); *C23C 16/308* (2013.01); *C23C 16/511* (2013.01); *Y10T 29/4913* (2015.01); *Y10T 436/206664* (2015.01)

(58) Field of Classification Search
CPC .......... G01N 31/12; G01N 31/00; G01N 1/22; G01N 1/02; G01N 1/00; G01N 1/405; G01N 1/40; G01N 1/28; G01N 33/0057; G01N 33/0036; G01N 33/0027; G01N 33/0009; G01N 27/12; G01N 27/04; G01N 27/02; Y10T 436/12; Y10T 436/00; C23C 16/308; C23C 16/30
USPC ............... 436/155, 135, 127; 422/98, 83, 50
See application file for complete search history.

(56) References Cited

U.S. PATENT DOCUMENTS

| | | |
|---|---|---|
| 7,011,737 B2 | 3/2006 | Varghese et al. |
| 2009/0085072 A1* | 4/2009 | Lee ............ G01N 27/4145 257/253 |

OTHER PUBLICATIONS

Piras, Frederica, M. et al, Silicon nitride and oxynitride films deposited from organosilicon plasma ToF-SIMs characterization with multivariate analysis, Surface & Coating Technology, 2008, 202, pp. 1606-1614.*
Storgaard-Larson, Torben, Plasma-Enhanced Chemical Vapor Deposition Silicon Oxynitride Films for Optical Waveguide Bridges for Use in Mechanical Sensors, J. Electrochem. Soc., Apr. 1997, vol. 44, No. 4, p. 1505-1513.*
Katrin Kneipp, et al., "Single Molecule Detection Using Surface-Enhanced Raman Scattering (SERS)," Mar. 3, 1997, Physical Review Letters, vol. 78, No. 9, pp. 1667-1670.
Shuming Nie, et al., "Probing Single Molecules and Single Nanoparticles by Surface-Enhanced Raman Scattering," Feb. 21, 1997, Science, New Series, vol. 275, No. 5303, pp. 1102-1106.
F. Dubnikova, et al., "Novel Approach to the Detection of Triacetone Triperoxide (TATP): Its Structure and Its Complexes with Ions," Apr. 18, 2002, The Journal of Physical Chemistry, American Chemical Society, vol. 106, No. 19, pp. 4951-4956.
Zhong-Qun Tian, et al., "Surface-Enhanced Raman Scattering: From Noble to Transition Metals and from Rough Surfaces to Ordered Nanostructures," Sep. 19, 2002, The Journal of Physical Chemistry, American Chemical Society, vol. 106, No. 37, pp. 9463-9483.
Yi-Sheng Lai, et al., "Evolution of Chemical Bonding Configuration in Ultrathin SiO x N y Layers Grown by Low-Temperature Plasma Nitridation," May/Jun. 2003, Journal of Vacuum Science & Technology A, American Vacuum Society, 21/3, pp. 772-778.
Subarna Banerjee, et al., "The Detection of Improvised Nonmilitary Peroxide Based Explosives Using a Titania Nanotube Array Sensor," Jan. 26, 2009, Nanotechnology 20, pp. 1-6.
A. Le Gouil, et al., "Gate Oxide Process Control Optimization by X-Ray Photoelectron Spectroscopy in a Semiconductor Fabrication Line," Jul./Aug. 2008, Journal of Vacuum Science & Technology A, American Vacuum Society, 26/805, pp. 805-811.

* cited by examiner

*Primary Examiner* — Christine T Mui
(74) *Attorney, Agent, or Firm* — Snell & Wilmer L.L.P.

(57) ABSTRACT

Functionalized titanium nanotubes can be utilized to detect compounds of interest, for example peroxide-based explosives. The nanotubes may desirably be coated, for example with a silicon oxynitride coating, in order to improve detection performance and/or functionality in the presence of moisture, saline, or other conditions typically unfavorable to titanium nanotube detection devices and methods. Inexpensive, compact, reusable, and responsive sensors may be fabricated from the coated nanotubes.

17 Claims, 6 Drawing Sheets

SOLID STATE SENSOR FOR DETECTION OF EXPLOSIVES

CROSS REFERENCE TO RELATED APPLICATIONS

This application claims priority to, and the benefit of, U.S. Provisional Application Ser. No. 61/730,780 entitled "SOLID STATE SENSOR FOR DETECTION OF EXPLOSIVES" and filed Nov. 28, 2012, the contents of which are incorporated herein by reference.

TECHNICAL FIELD

The present disclosure relates to sensors, and in particular to detection of explosives in connection with nanotube sensors.

BACKGROUND

Many security approaches, for example parcel and passenger screening at airports, utilize devices configured to detect trace amounts of explosive material. However, there are thousands of explosive compounds that may be utilized in a malicious manner, and no single approach is capable of detecting every such compound. Additionally, various explosive precursors may not be detectable by a particular device configured to detect the final explosive compounds.

Moreover, certain existing sensors, for example nanotube sensors utilizing titanium dioxide nanotubes, can suffer degradation of performance or become inoperable under certain common operating conditions, for example when exposed to moisture and/or saline vapor. Accordingly, improved nanotube sensors remain desirable, particularly in connection with detection of explosive compounds or other molecules of interest.

SUMMARY

In an exemplary embodiment, a sensor comprises a titanium nanotube functionalized to react to a peroxide-based explosive, a silicon oxynitride coating disposed on the titanium nanotube, and an electrical component configured to detect a change in the conductance of the titanium nanotube responsive to the presence of the peroxide-based explosive.

In another exemplary embodiment, a method of forming a sensor comprises forming a titanium nanotube on a titanium substrate, functionalizing the titanium nanotube with a metal ion, coating the titanium nanotube with silicon oxynitride, and coupling an electrical component to the titanium nanotube to detect a change in the conductance of the titanium nanotube responsive to the presence of a compound of interest.

In another exemplary embodiment, a method of detecting a peroxide-based explosive comprises providing a titanium nanotube functionalized to react to the peroxide-based explosive, the titanium nanotube having a silicon oxynitride coating disposed thereon, exposing the titanium nanotube to a source of the peroxide-based explosive, and measuring a change in the conductance of the titanium nanotube to detect the presence of the peroxide-based explosive.

BRIEF DESCRIPTION OF THE DRAWINGS

With reference to the following description and accompanying drawings.

DETAILED DESCRIPTION

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from principles of the present disclosure.

For the sake of brevity, conventional techniques for nanotube fabrication and/or functionalization, sensor calibration, electronics fabrication, and the like may not be described in detail herein. Furthermore, the connecting lines shown in various figures contained herein are intended to represent exemplary functional relationships and/or physical couplings between various elements. It should be noted that many alternative or additional functional relationships or physical connections may be present in a practical nanotube-based sensor system, for example an explosive detection system.

Prior sensor devices and systems suffer from various deficiencies. For example, certain titanium nanotube based sensors suffer from degraded performance and/or are rendered inoperable in the presence of moisture or saline vapor. However, areas where explosive detection is desirable, such as ports, coastlines, and/or the like, are often moist, damp, and/or saline. Accordingly, such detectors are unsuitable for use in these areas, or offer unsatisfactory performance when utilized therein.

In contrast, these and other shortcomings of prior approaches may be overcome by utilizing principles of the present disclosure, for example as illustrated in various exemplary embodiments. For example, by utilizing titanium nanotubes having a silicon oxynitride coating, improved sensor performance in the presence of moisture and/or salinity may be achieved. As compared to prior titanium nanotube sensors, a sensor system configured in accordance with principles of the present disclosure allows detection of a desired target compound while remaining functional in the presence of moisture and/or saline vapor.

Figure 1A:
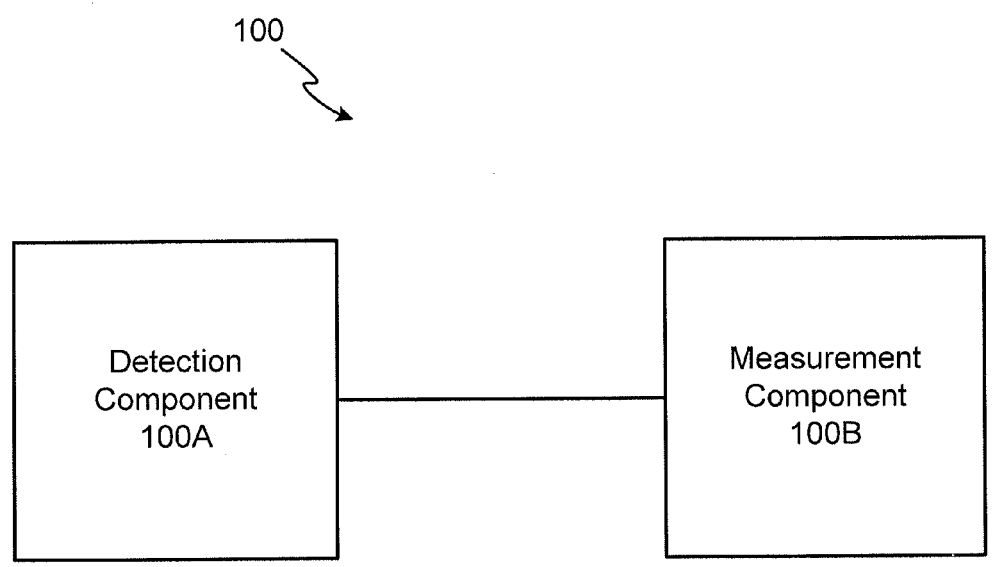
FIG. 1A is a block diagram of an exemplary explosive detection system in accordance with an exemplary embodiment.

As used herein, an explosive detection system may be any system configured to facilitate detection of a desired chemical compound or compounds, for example a peroxide-based explosive such as TATP (triacetone triperoxide) or HMTD (hexamethylene triperoxide). In accordance with an exemplary embodiment, and with reference to FIG. 1A, an explosive detection system 100 generally comprises a detection component 100A and a measurement component 100B. Detection component 100A is configured to reversibly vary a characteristic of detection component 100A, for example a resistance, conductance, voltage, current, capacitance, and/or the like, responsive to the presence of a target compound. Measurement component 100B is coupled to detection component 100A and is configured to characterize, control, interpret, compute, and/or otherwise process information obtained from and/or via detection component 100A.

Figure 1B:
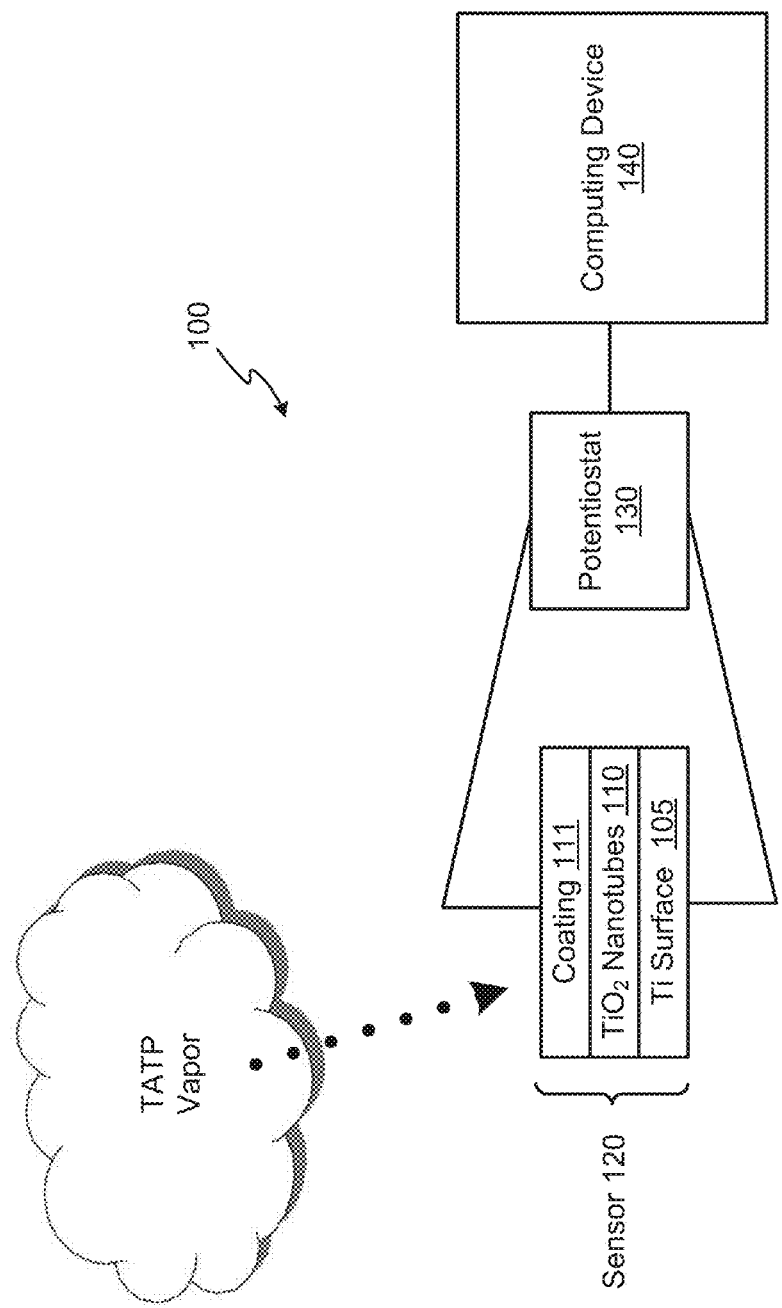
FIG. 1B is a block diagram of an exemplary explosive detection system in accordance with an exemplary embodiment.

In an exemplary embodiment, with reference to FIG. 1B, an exemplary explosive detection system 100 comprises detection component 100A (e.g., surface 105 coupled to titanium nanotubes 110 to form sensor 120) and measurement component 100B (e.g., potentiostat 130 coupled to computing device 140). Moreover, explosive detection system 100 may comprise any suitable components and/or configurations for detecting an explosive compound or compounds. In an exemplary embodiment, an exemplary explosive detection system 100 comprises a titanium nanotube functionalized to react to a peroxide-based explosive, a silicon oxynitride coating disposed on the titanium nanotube, and an electrical component configured to detect a change in the conductance of the titanium nanotube responsive to the presence of the peroxide-based explosive.

Surface 105 comprises any suitable surface, layer, substrate, and/or the like for growth and/or deposition of nanotubes, for example titanium nanotubes. In various exemplary embodiments, surface 105 comprises a polished titanium surface. In other exemplary embodiments, surface 105 comprises a titanium layer deposited on a silicon substrate, for example via ultrahigh vacuum deposition.

In various exemplary embodiments, a plurality of nanotubes 110 may be grown on surface 105. Nanotubes 110 may comprise titania, anatase, and/or other titanium compounds and/or crystalline structures as is known in the art. Moreover, nanotubes 110 may comprise and/or be modified, sensitized, and/or functionalized with other suitable compounds or materials, as desired, for example in order to modify and/or control the dimensions or other characteristics of nanotubes 110.

In certain exemplary embodiments, nanotubes 110 are modified with metal ions, for example zinc (Zn) ions. In other exemplary embodiments, nanotubes 110 are modified with one or more of silver (Ag), cadmium (Cd), tin (Sn), and/or antimony (Sb). In various exemplary embodiments, nanotubes 110 are modified with one or more transition metals, for example iron (Fe), cobalt (Co), nickel (Ni), and/or the like. In various exemplary embodiments, nanotubes 110 may be modified, sensitized, and/or functionalized with a desired first compound and/or material in order to react and/or respond to a desired second compound and/or material.

In various exemplary embodiments, nanotubes 110 have a length of between about 300 nanometers (nm) and about 2000 nm (2 microns). In certain embodiments, nanotubes 110 are configured with an outer diameter of between about 20 nm and about 60 nm. Nanotubes 110 may be configured with any suitable lengths, diameters, and/or other dimensions in order to facilitate use of nanotubes 110 in connection with detection of one or more compounds.

In various exemplary embodiments, nanotubes 110 may be coated and/or otherwise modified with a coating 111. Nanotubes 110 may be coated and/or modified in order to vary one or more characteristics, for example response to an explosive compound, humidity, saline vapor, and/or the like.

In certain exemplary embodiments, nanotubes 110 are coated with silicon oxynitride. Silicon oxynitride coating 111 desirably provides a stable barrier to moisture, sodium ions, and other chemicals which may disrupt the sensitivity of explosive detection system 100. Coating 111 (e.g., of silicon oxynitride) may be configured in any suitable manner. In certain exemplary embodiments, the silicon oxynitride layer comprising coating 111 is between about 8 nm and about 25 nm thick. In other exemplary embodiments, the silicon oxynitride layer comprising coating 111 is between about 9 nm and about 13 nm thick. Coating 111 may be primarily disposed on the outer walls of nanotubes 110; moreover, coating 111 may also be disposed on the inner walls of nanotubes 110.

In various other embodiments, coating 111 comprises one or more of silicon nitride, silicon oxides, and/or the like.

In various exemplary embodiments, sensor 120 comprises a plurality of nanotubes 110. In an exemplary embodiment, in sensor 120 an array of nanotubes 110 are generally vertically aligned extending from surface 105. However, nanotubes 110 may be aligned, grouped, oriented, and/or otherwise configured in a manner or manner(s) suitable to allow nanotubes 110 or materials therein to react with compounds present in the ambient environment.

Figure 2:
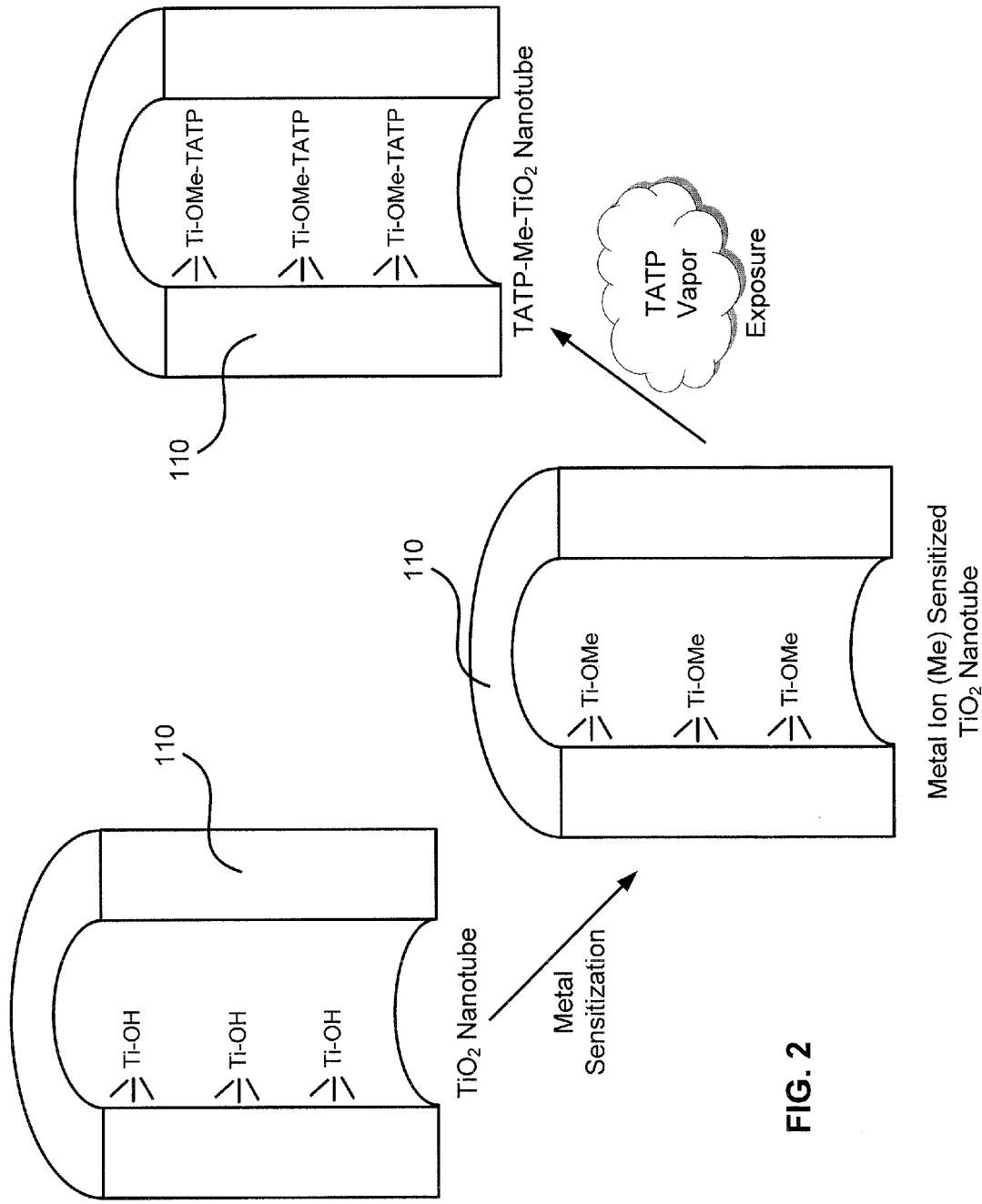
FIG. 2 illustrates titanium nanotubes configured and used for sensing in accordance with an exemplary embodiment.
Figure 4:
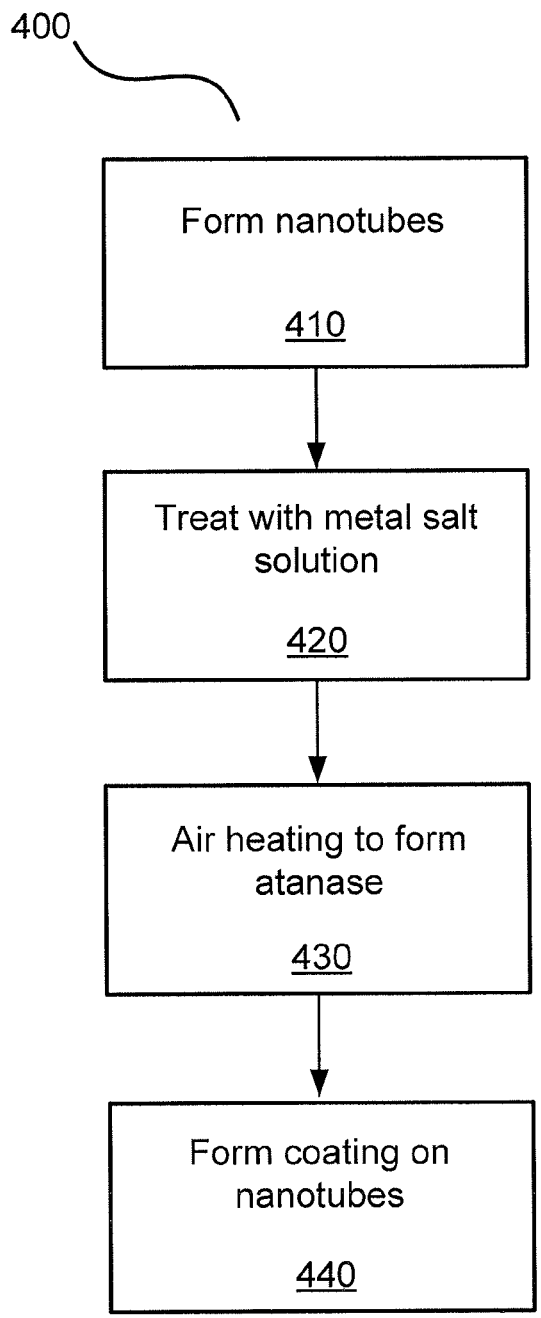
FIG. 4 illustrates a process for fabrication of coated nanotubes in accordance with an exemplary embodiment.

In certain exemplary embodiments, with reference now to FIGS. 2 and 4, nanotubes 110 may be formed via a process 400. In process 400, nanotubes 110 are fabricated on surface 105 by electrolytic oxidation of titanium in a suitable bath as is known in the art (step 410). Nanotubes 110 are treated with a metal salt solution (for example, a water soluble zinc salt solution, a chloride solution, a sulfate solution, a carboxylate solution, and/or the like) for a period of between about 1 hour and about 6 hours at a temperature of between about 90° C. and about 110° C. (step 420). In this manner, nanotubes 110 are sensitized for detection as illustrated in FIG. 2. The zinc treated nanotubes 110 are heated in air at a temperature of at least 200° C. but less than 550° C. for a period of between about 1 hour and about 6 hours in order to convert at least a portion of the titania in nanotubes 110 to anatase (step 430). It will be appreciated that exceeding the maximum temperature in step 430 will convert at least a portion of the titania to rutile, which is undesirable.

Nanotubes 110 are next coated with a suitable coating 111, for example silicon oxynitride (step 440). In various exemplary embodiments, nanotubes 110 are coated with coating 111 via plasma-enhanced chemical vapor deposition (PECVD). However, other suitable processes for deposition of coating 111 may also be utilized.

In an exemplary embodiment, sensor 120 (comprising nanotubes 110 on substrate 105) is placed in a 2.3 Ghz microwave PECVD instrument or other suitable PECVD device. The instrument chamber is configured with a temperature of between about 190° C. and about 210° C. (and preferably, about 200° C.) and a pressure of less than about 1000 mTorr (and preferably, about 550 mTorr).

In the PECVD process, any suitable materials and/or compositions may be utilized in order to facilitate creation of the silicon oxynitride coating 111 on nanotubes 110. In various exemplary embodiments, a microwave plasma of silane ($SiH_4$) and ammonia ($NH_3$) may be utilized. In one exemplary embodiment, the PECVD process may utilize helium (He) at about 1000 standard cubic centimeters per minute (sccm), $NH_3$ at about 70 sccm, nitrous oxide ($N_2O$) at about 15 sccm, and $SiH_4$ at about 15 sccm. In various exemplary embodiments, the PECVD process may utilize He at between about 900 sccm and about 1100 sccm, $NH_3$ at between about 63 sccm and about 77 sccm, $N_2O$ at between about 13 sccm and about 17 sccm, and $SiH_4$ at between about 13 sccm and about 17 sccm. However, any suitable materials, concentrations, and flow rates may be utilized in the formation of coating 111.

A deposition time of between about 80 seconds and about 100 seconds (and preferably, about 85 seconds) may be utilized in order to form a coating 111 having a suitable thickness of between about 8 nm and about 25 nm.

In various exemplary embodiments, electrical connections to sensor 120 may be applied at any suitable time during process 400. In one exemplary embodiment, wires may be coupled to sensor 120 after the heating in air (step 430) but before the high vacuum annealing (step 440). In another exemplary embodiment, wires may be coupled to sensor 120 after the high vacuum annealing (step 440). Additionally, other components of sensor 120 or additional components coupled thereto (for example, a micro-electromechanical circuit or the like) may be incorporated into sensor 120 or coupled thereto at any suitable time, either before, during, or after completion of process 400.

In various exemplary embodiments, silicon oxynitride coating 111 resulting from process 400 may be between about 8 nm and about 25 nm thick. Coating 111 may comprise SiO1.24NO.3 with between about 13% H and about 17% H. Additionally, coating 111 may comprise some SiON on $SiO_2$. A small quantity of carbon may also be present; the carbon may be reduced by sputtering as is known in the art.

Nanotubes 110 configured with coating 111 in accordance with principles of the present disclosure may be characterized via any suitable method or devices. In an exemplary embodiment, nanotubes 110 may be characterized by scanning transmission electron microscopy (TEM) collecting energy dispersive X-ray signals (STEM/EDS) and dark field (DF) images, for example obtained by a FEI CM 300 FEG operating at 297 kV and using the Emispec program ES Vision and an Oxford ultra-thin window light element detector. TEM samples may be prepared by scraping off nanotubes 110 onto a carbon support film, for example a film configured with 200 mesh Cu grids. X-ray images may be generated by placing regions of interest windows at desired locations, for example around the Ti Ka and the Pt Ma peaks. A suitable dwell time, for example 1 sec per pixel, may be used in order to collect sufficient compositional contrast.

Figure 3:
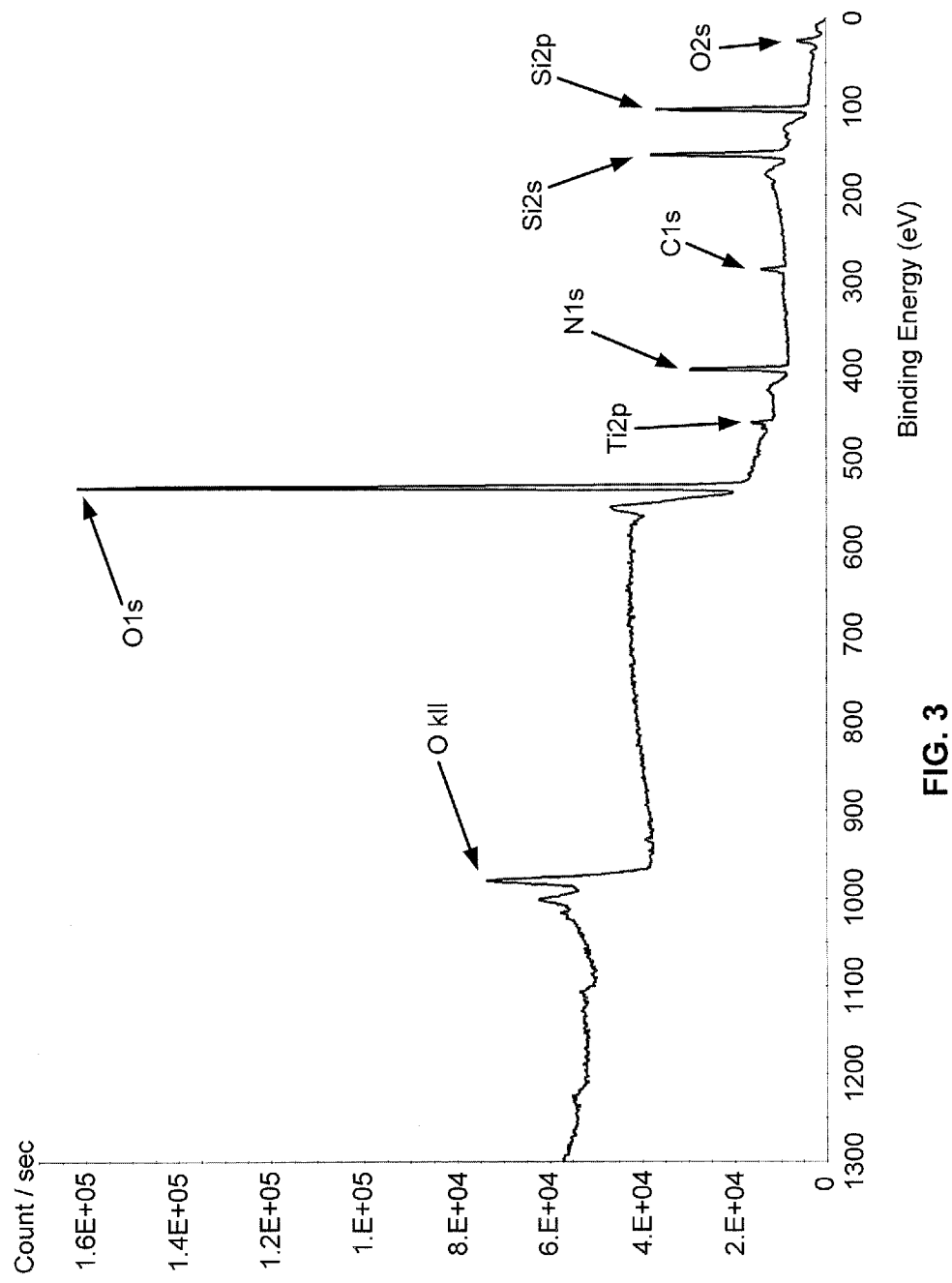
FIG. 3 illustrates raw x-ray photoelectron spectroscopy (XPS) data of silicon oxynitride coated titanium nanotubes in accordance with an exemplary embodiment.

In various exemplary embodiments, nanotubes 110 configured with coating 111 may be characterized via x-ray photoelectron spectroscopy (XPS). With reference to FIG. 3, exemplary nanotubes 110 configured with coating 111 and characterized via XPS show XPS core levels for $Si_{2p}$, $N_{1s}$, $O_{1s}$, with $Ti_{2p}$, together with some $C_{1s}$ due to impurity.

In accordance with various exemplary embodiments, exemplary nanotubes 110 configured with coating 111 in accordance with principles of the present disclosure may be characterized using Fourier transform infrared spectroscopy (FTIR). FTIR spectra of exemplary nanotubes 110 taken with an advanced glazing angle (approx. 85 degrees) shows peaks at 808, 939, 1069 and 1230-1278 reciprocal centimeters ($cm^{-1}$). These peaks correspond with Si—O bending, Si—N assymetrical stretch, Si—O—Si stretching, and SiCH2 (CH assymetrical bending), respectively.

Sensor 120 may be coupled to any suitable components or devices in order to utilize the sensing capabilities of sensor 120. In various exemplary embodiments, sensor 120 is coupled to potentiostat 130.

With reference again to FIG. 1B, in various exemplary embodiments, potentiostat 130 may be any device configured to evaluate, monitor, respond to, quantify, or otherwise assess a change in a characteristic of sensor 120. In certain exemplary embodiments, potentiostat 130 comprises an EG&G Model 283 potentiostat from Princeton Applied Research. In other exemplary embodiments, potentiostat 130 comprises a potentiostat offered by Uniscan Instruments corporation. However, any suitable potentiostat 130 may be utilized.

In various exemplary embodiments a conductive connection, for example a silver epoxy, may be utilized to couple an electrical wire between surface 105 and potentiostat 130. Similarly, a conductive connection may be utilized to couple an electrical wire between nanotubes 110 and potentiostat 130. In this manner, a complete electrical circuit is formed, allowing potentiostat 130 to monitor changes in one or more characteristics of sensor 120, for example conductance.

In various exemplary embodiments, potentiostat 130 is coupled to computing device 140 via a suitable means, for example a wire. Potentiostat 130 may also be coupled to or incorporate wireless communication components, for example in order to provide remote detection and/or monitoring capabilities.

In various exemplary embodiments, computing device 140 may take the form of a personal computer, server, mobile phone, personal digital assistant, tablet, laptop, notebook, netbook, and/or the like. In other exemplary embodiments, computing device 140 may take the form of an embedded system, system-on-a-chip, microprocessor, microcontroller, and/or the like. Computing device 140 may be configured with memory and/or storage to record the output of sensor 120 and/or potentiostat 130. Computing device 140 may also be configured with wired and/or wireless communication capabilities, for example utilizing common networking protocols, in order to communicate with other computing devices 140 or other electronic devices.

It will be appreciated that in certain exemplary embodiments, the functions and/or components of potentiostat 130 and computing device 140 may be combined in a single device.

Figure 5:
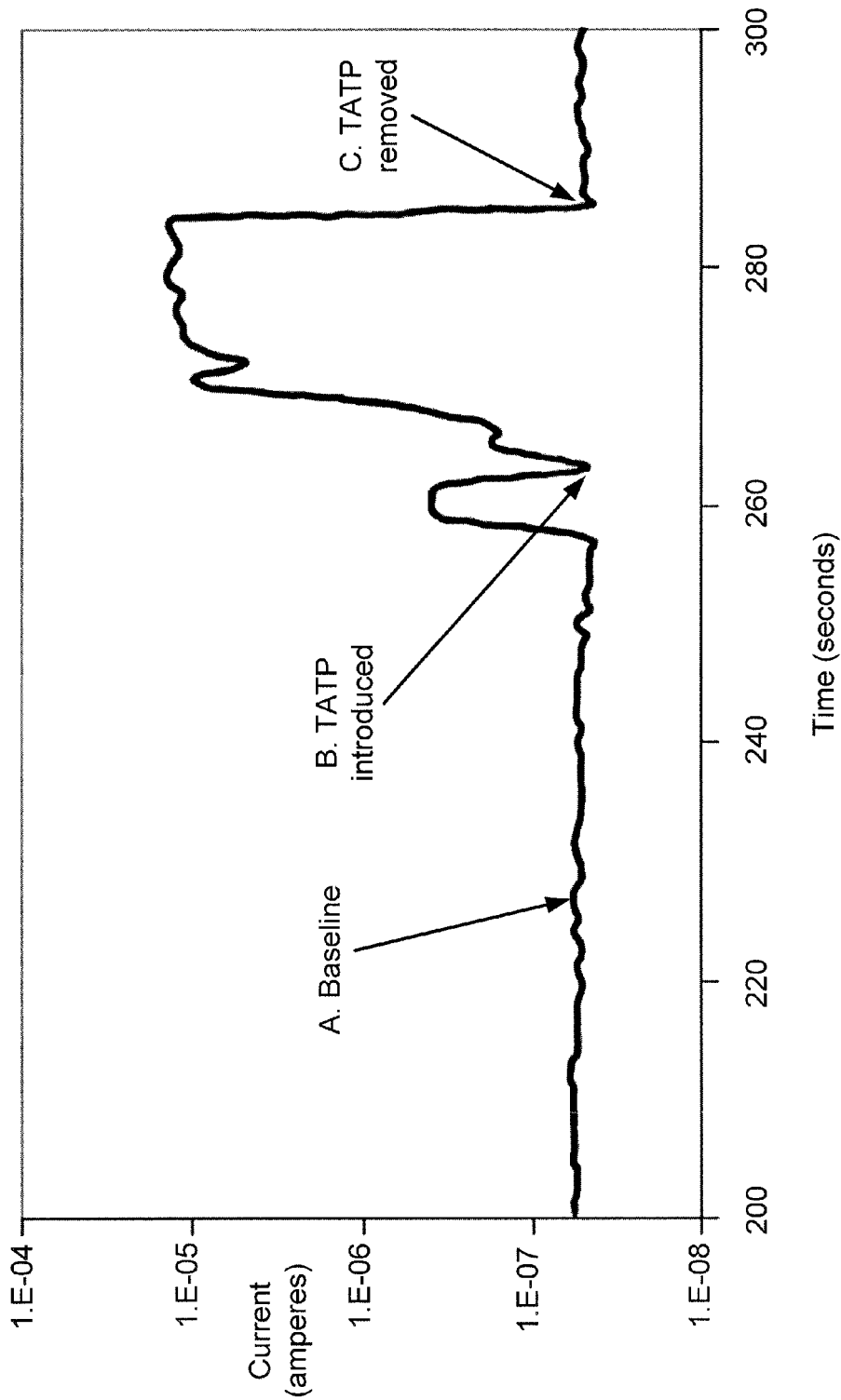
FIG. 5 illustrates operational output of an exemplary explosive detection system utilized to detect triacetone triperoxide (TATP) accordance with an exemplary embodiment.

In an exemplary embodiment, with reference now to FIG. 5, explosive detection system 100 is operable to detect a peroxide-based explosive, for example TATP. Sensor 120 of explosive detection system 100 is exposed to ambient air, and potentiostat 130 detects a baseline level of current flowing through sensor 120 (illustrated at time A in FIG. 5). At time B, sensor 120 is exposed to ambient air having a trace amount of TATP therein (in the operation depicted in FIG. 5, TATP ambient vapor pressure was about 0.005 mm of mercury (Hg) or about 5 Pascals (PA)). Within only a few seconds, current through sensor 120 increases rapidly responsive to the change in conductance in nanotubes 110 arising from exposure to TATP (resulting from formation of labile complexes). The resulting change in conductance provides a strong and unambiguous "positive" test result for TATP presence. At time C, the TATP source is removed, and current through sensor 120 rapidly falls back to the baseline level. Sensor 120 is then ready to detect a subsequent TATP exposure.

Via application of principles of the present disclosure, a compact, inexpensive, sensitive, reusable explosive detection system 100 is facilitated. It will be appreciated that principles of the present disclosure may suitably be applied for high-volume fabrication of nanosensors; the resulting sensors may be cost-effectively incorporated into portable and/or ubiquitous devices (e.g., pens, watches, jewelry, portable electronics, and/or the like) in order to provide broad sensor coverage and potential early detection of unlawful uses of various explosive compounds.

Table 1 presents XPS results for exemplary nanotubes 110 configured with coating 111 in accordance with principles of the present disclosure.

TABLE 1

| Name | Start BE | Peak BE | End BE | Height Counts | FWHM eV Area (P) | CPS.eV Area (non-normalized) | Normalized Area | At % |
|---|---|---|---|---|---|---|---|---|
| Si2p | 108.50 | 103.69 | 98.20 | 26003.56 | 3.93 | 110627.02 | 117.78 | 27.44 |
| C1s | 292.00 | 285.86 | 282.10 | 2637.39 | 4.19 | 12413.03 | 11.75 | 2.74 |
| N1s | 403.00 | 399.01 | 395.00 | 13699.45 | 3.72 | 55340.36 | 30.89 | 7.20 |
| O1s | 538.00 | 533.09 | 527.70 | 110253.42 | 3.83 | 462869.15 | 171.75 | 40.02 |
| Ti2p | 469.00 | 459.37 | 455.20 | 4055.47 | 3.91 | 23885.59 | 3.14 | 0.73 |

Table 2 presents XPS results and analysis for various exemplary sensors 120 configured in accordance with principles of the present disclosure.

TABLE 2

| Ref. | Name | Peak BE | Height CPS | Height Ratio | Area CPS.eV | Area Ratio | FWHM eV |
|---|---|---|---|---|---|---|---|
| Sensor I | O1s | 533.06 | 9274.45 | 1.00 | 16240.42 | 1.00 | 1.68 |
| Sensor J | O1s A | 532.41 | 1512.06 | 0.16 | 1953.68 | 0.12 | 1.24 |
| Sensor K | O1s B | 531.20 | 716.03 | 0.08 | 1268.36 | 0.08 | 1.70 |
| Sensor C | Si2p | 103.74 | 1738.87 | 1.00 | 3546.79 | 1.00 | 1.96 |
| Sensor D | Si2p A | 102.87 | 203.58 | 0.12 | 415.76 | 0.12 | 1.96 |
| Sensor E | N1s | 399.03 | 1117.33 | 1.00 | 1990.29 | 1.00 | 1.71 |
| Sensor F | N1s A | 400.20 | 108.01 | 0.10 | 193.54 | 0.10 | 1.72 |

Table 3 presents Rutherford backscatter assessment for exemplary nanotubes 110 configured with coating 111 in accordance with principles of the present disclosure.

TABLE 3

| Sample | Si | O | N | H | Ti |
|---|---|---|---|---|---|
| Sample 1 | .12 | .50 | .07 | .13 | .17 |
| Sample 2 | .13 | .56 | .02 | .14 | .13 |

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure.

The present disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection.

What is claimed is:

1. A chemical sensor for a peroxide-based explosive, the sensor comprising:
   a titanium nanotube functionalized to react to a peroxide-based explosive;
   a silicon oxynitride coating disposed on the titanium nanotube to provide a barrier to sodium ions, wherein the silicon oxynitride coating is configured with a thickness of between 8 nm and 25 nm; and
   an electrical component configured to detect a change in the conductance of the titanium nanotube responsive to the presence of the peroxide-based explosive.

2. The sensor of claim 1, wherein the titanium nanotube is functionalized with a zinc ion.

3. The sensor of claim 1, wherein the sensor comprises a plurality of titanium nanotubes.

4. The sensor of claim 1, wherein the peroxide-based explosive is at least one of triacetone triperoxide (TATP) or hexamethylene triperoxide (HMTP).

5. A method of forming a chemical sensor for a peroxide-based explosive, the method comprising:
   forming a titanium nanotube on a titanium substrate;
   functionalizing the titanium nanotube with a metal ion;
   coating the titanium nanotube with silicon oxynitride having a thickness of between 8 nm and 25 nm to provide a barrier to sodium ions; and
   coupling an electrical component to the titanium nanotube to detect a change in the conductance of the titanium nanotube responsive to the presence of a compound of interest.

6. The method of claim 5, wherein the compound of interest is a peroxide-based explosive.

7. The method of claim 5, wherein the metal ion is zinc.

8. The method of claim 5, wherein the silicon oxynitride is formed via plasma-enhanced chemical vapor deposition (PECVD).

9. The method of claim 8, wherein the PECVD is conducted at a temperature between 190 degrees Celsius and 210 degrees Celsius.

10. The method of claim 8, wherein the PECVD is conducted at a pressure of less than 1000 mTorr.

11. The method of claim 8, wherein the PECVD deposition time is between 80 seconds and 100 seconds.

12. A method of detecting the presence of a peroxide-based explosive, the method comprising:
providing a chemical sensor comprising a titanium nanotube functionalized to react to the peroxide-based explosive, the titanium nanotube having a silicon oxynitride coating having a thickness of between 8 nm and 25 nm disposed thereon to provide a barrier to sodium ions;
exposing the titanium nanotube to a source of the peroxide-based explosive; and
measuring a change in the conductance of the titanium nanotube to detect the presence of the peroxide-based explosive.

13. The method of claim 12, wherein the silicon oxynitride coating is formed via plasma-enhanced chemical vapor deposition (PECVD).

14. The method of claim 13, wherein the PECVD is conducted at a temperature between 190 degrees Celsius and 210 degrees Celsius.

15. The method of claim 13, wherein the PECVD is conducted at a pressure of less than 1000 mTorr.

16. The method of claim 13, wherein the PECVD deposition time is between 80 seconds and 100 seconds.

17. The method of claim 12, further comprising communicating, via a computing device coupled to the titanium nanotube, the detection of the peroxide-based explosive.

* * * * *